United States Patent [19]

Chevallet

[11] Patent Number: 4,923,613

[45] Date of Patent: May 8, 1990

[54] METHOD FOR DETERMINING A PATIENT'S BLOOD SODIUM LEVEL AND ARTIFICIAL KIDNEY FOR THE APPLICATION THEREOF

[75] Inventor: Jacques Chevallet, Serezin du Rhone, France

[73] Assignee: Hospal Industrie, Cedex, France

[21] Appl. No.: 192,657

[22] Filed: May 11, 1988

[30] Foreign Application Priority Data

May 15, 1987 [FR] France ................................. 87 07017

[51] Int. Cl.$^5$ .......................... B01D 13/00; A61M 1/16
[52] U.S. Cl. ...................................... 210/647; 210/85;
210/138; 210/143; 210/321.65; 210/321.71;
210/321.72; 72/61.1 R
[58] Field of Search ........................................ 604/4–6;
210/85, 138, 143, 195.2, 321.65, 321.71, 321.72,
647, 929; 73/53, 61.1 R; 324/438, 439

[56] References Cited

U.S. PATENT DOCUMENTS 4,668,400 5/1987 Veech ................................. 210/647

OTHER PUBLICATIONS

"Clinical Validation of a Predictive Modeling Equation for Sodium," Artificial Organs, Nguyen-Khoa et al., Raven Press, New York 1985.

"Theorie et Pratique de law Modelisation Des Transferts Sodes Lors de la Seance D'Hemodialyse," dated 6/13/85, by Dr. Thierry Petitclerc.

Primary Examiner—W. Gary Jones
Attorney, Agent, or Firm—Finnegan, Henderson Farabow, Garrett & Dunner

[57] ABSTRACT

A method for determining the blood sodium level of a patient whose blood circulates through one compartment of an exchanger separated from a dialysis fluid by a semipermeable membrane, wherein the conductivity of the dialysis fluid of equilibrium with the plasma is determined by: changing in a selected manner the conductivity of the dialysis fluid at inflow the exchanger, measuring the conductivity of the dialysis fluid at outflow from the exchanger, determining a lag time $t_L$ of the change in conductivity of dialysis fluid between inflow to and outflow from the exchanger, and determining an equilibrium conductivity value of the dialysis fluid for which the conductivity at outflow from the exchanger at an instant t is equal to the conductivity at inflow at an instant $t - t_L$. The invention also relates to an artificial kidney incorporating means for carrying out this method.

15 Claims, 6 Drawing Sheets

METHOD FOR DETERMINING A PATIENT'S BLOOD SODIUM LEVEL AND ARTIFICIAL KIDNEY FOR THE APPLICATION THEREOF

BACKGROUND OF THE INVENTION

1. Field of the Invention

The present invention relates to the technical field of analysis of blood circulating in an apparatus which provides for its purification, and which is commonly known as an artificial kidney. More particularly, the present invention relates to a method by means of which the sodium concentration in the blood may be determined, as well as to an artificial kidney incorporating means that provide for the implementation of this method.

2. Description of the Related Art

The purification of blood by means of an artificial kidney employs different modes of exchange between the blood and a purification fluid known as the dialysis fluid. These exchanges take place through a semipermeable membrane enabling the blood to be purified both by dialysis and by ultrafiltration.

The phenomenon of dialysis or diffusion is a consequence of the difference in concentration of solutes existing between the blood and the dialysis fluid. Substances present in the blood at a larger concentration than in the dialysis fluid tend to pass through the membrane of the exchanger until concentration equilibrium is established. Thus, if it is desired to eliminate certain substances present in excess in the blood, a dialysis fluid which is devoid thereof is circulated on the other side of the membrane. Conversely, if it is desired to enrich the blood with respect to a given substance, a dialysis fluid is chosen whose concentration of this substance is larger than that in the blood.

The second mode of purification used in an artificial kidney is ultrafiltration, which is the consequence of the pressure difference existing between the two fluids on each side of the membrane. In the case where the pressure of the blood is greater than the pressure of the dialysis fluid, a portion of the aqueous fraction of the blood passes through the semipermeable membrane and is then eliminated with the dialysis fluid.

This ultrafiltration phenomenon enables, in particular, the patient's excess water load to be abolished. In effect, in a chronic haemodialysed patient, the water which should normally be eliminated via the kidneys accumulates in the body between two haemodialysis sessions. This water excess is distributed between the intracellular compartment and the extracellular compartment including, in particular, the vascular system.

Although, during the haemodialysis session, the only compartment directly accessible is the vascular medium, it is not possible to abolish the patient's excess water load completely by simple ultrafiltration of the blood. This would, in effect, very quickly incur the risk of producing blood pressure drops in the patient, due to the decrease in blood volume. Moreover, if the aim is no more than to correct the extracellular hyperhydration, the well known syndrome of imbalance, which results, in particular, in headaches, nausea and cramp, is produced in the patient.

It is hence of importance, during the haemodialysis session, not only to achieve the desired weight loss, but also to monitor the water balance between the different compartments of the body.

One of the factors enabling this water balance to be monitored is the patient's blood sodium level. The doctor who supervises the progress of the haemodialysis session consequently needs to monitor the patient's blood sodium level so that the blood treatment conditions can then be modified if necessary.

In order to determine the value of a patient's blood sodium level, it is known, according to the prior art, to draw venous blood samples and then analyze them, by means of a sodium-specific electrode for example.

Although reliable, this method has, however, the drawback of being tedious and expensive on account, in particular, of the large number of calibrations required. It is not, moreover, advisable to draw too many blood samples from a haemodialysed patient who is, in general, already suffering from anaemia.

To remedy these drawbacks, Dr. Petitclerc proposes, in his thesis of 13th June 1985, entitled "Theoretical Approach and Clinical Application of Sodium Modeling During Haemodialysis," to replace the measurement of blood sodium level by a measurement of the conductivity of the dialysis fluid in equilibrium with the blood plasma. Dr. Petitclerc describes in his thesis a very good correlation existing between these two values.

In order to achieve equilibrium between the plasma and the dialysis fluid, Dr. Petitclerc proposes the recirculation of a small amount of dialysis fluid into the exchanger, until equilibrium, or an approximation thereof, is obtained. This recirculation stage lasts for approximately 10 minutes, and must be performed at each fresh measurement. During this recirculation stage, the ultrafiltration is maintained at its nominal rate.

This method for obtaining equilibrium between the dialysis fluid and the blood plasma has a very serious drawback. In effect, at each measurement stage, the purification of the blood by dialysis is very rapidly limited as a result of the recirculation of the dialysis fluid. Thus, in the case where it is desired to perform frequent determinations of the blood sodium level, the purification of the blood by dialysis becomes insufficient if the length of the haemodialysis session is not extended.

To enable good purification of the blood to be achieved by dialysis, it is hence necessary either to extend the length of the blood treatment or to limit the number of measurements performed. Whichever alternative is chosen, the solution is in no way satisfactory.

The object of the present invention is therefore to remedy the drawbacks of the prior art and to propose a method and an artificial kidney by means of which a patient's blood sodium level may be determined simply, rapidly, reliably and at low cost.

Another object of the present invention is to propose a method and an artificial kidney by means of which a patient's blood sodium level may be determined without the need to draw a sample of venous blood.

Another object of the present invention is to propose a method and an artificial kidney by means of which a patient's blood sodium level may be determined as frequently as desired.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

To achieve the above-mentioned objects, the subject of the present invention is a method for determining the blood sodium level of a patient whose blood circulates through a first compartment of an exchanger of an artificial kidney. A dialysis fluid flowing in a dialysis fluid circuit passes through a second compartment of the exchanger which is separated from the first compartment by a semipermeable membrane for permitting the dialysis and ultrafiltration of the blood. The method comprises the steps of changing, in a selected manner, the conductivity of the dialysis fluid flowing into the second compartment of the exchanger; measuring the conductivity of the dialysis fluid flowing out of the second compartment of the exchanger; determining a lag time $t_L$ of the change in conductivity of the dialysis fluid between inflow to and outflow from the second compartment of the exchanger; determining an equilibrium conductivity value of the dialysis fluid for which the conductivity at outflow from the second compartment at an instant t is substantially equal to the conductivity of the dialysis fluid at inflow into the second compartment of an instant $t' = t - t_L$; and determining the sodium concentration in the plasma in accordance with the determined equilibrium conductivity value.

The subject of the present invention is also an artificial kidney comprising an exchanger having at least two compartments separated by a semipermeable membrane permitting the dialysis and ultrafiltration of the blood, the first compartment being disposed in an extracorporeal blood circuit and the second compartment being disposed in a dialysis fluid circuit through which dialysis fluid flows. The dialysis fluid circuit includes means for changing, in a selected manner, the conductivity of the dialysis fluid flowing into the second compartment of the exchanger and means for measuring the conductivity of the dialysis fluid flowing out of the second compartment. The artificial kidney further comprises means for determining a lag time $t_L$ of between a change in conductivity of the dialysis fluid flowing into the second compartment and the corresponding change in conductivity of the dialysis fluid measured by the measuring means at outflow from the second compartment; and means for determining an equilibrium conductivity value of the dialysis fluid and the plasma for which equilibrium value the conductivity of the dialysis fluid flowing out of the second compartment at an instant t is substantially equal to the conductivity of the dialysis fluid flowing into the second compartment at an instant $t' = t - t_L$.

Other objects and advantages of the present invention will emerge in the course of the description which follows, reference being made to the attached figures which illustrate, diagrammatically and on an unspecified scale, embodiments of the present invention.

BRIEF DESCRIPTION OF THE DRAWINGS

The accompanying drawings, which are incorporated in and constitute a part of the specification, illustrate a presently preferred embodiment and method of the invention and, together with the general description given above and the detailed description of the preferred embodiment and method given below, serve to explain the principles of the invention.

DESCRIPTION OF THE PREFERRED EMBODIMENTS AND METHOD

Figure 1:
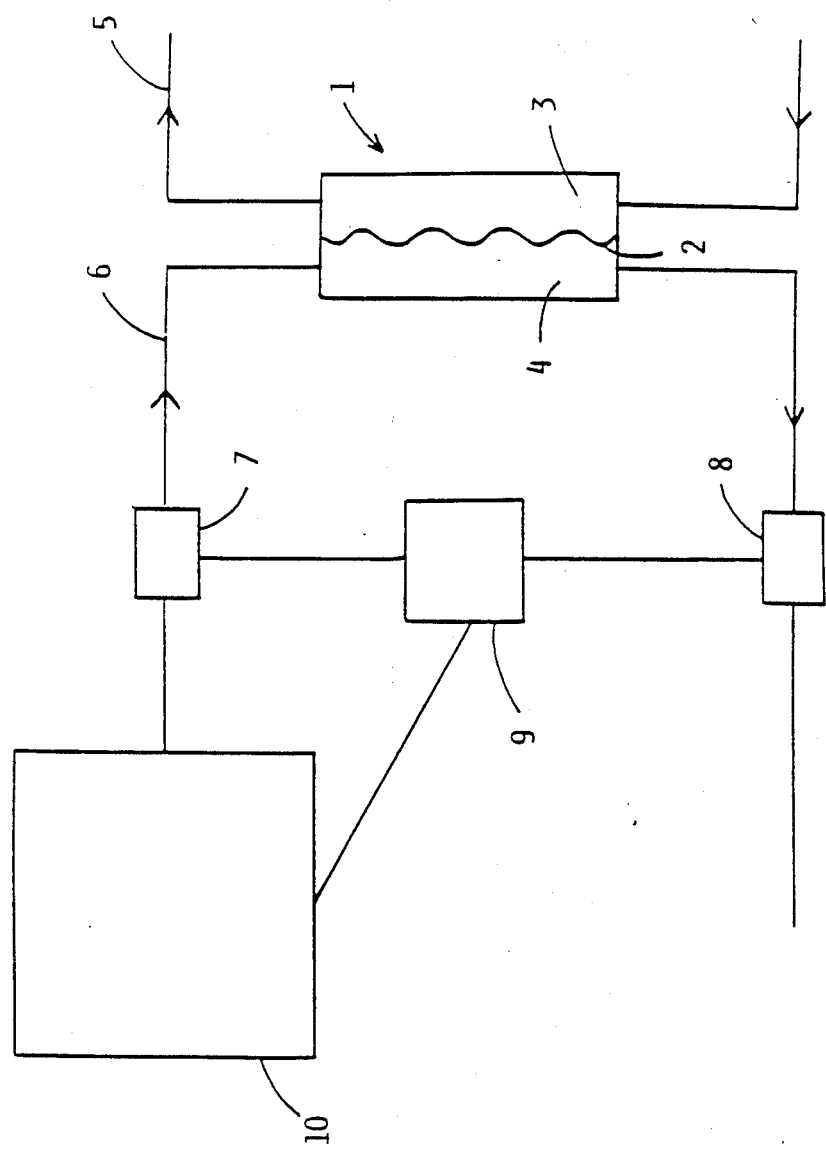
FIG. 1 illustrates schematically an embodiment of the artificial kidney which is the subject of the present invention.

Reference will now be made in detail to the presently preferred embodiments and method of the invention as illustrated in the accompanying drawings, in which like reference characters designate like or corresponding parts throughout the several drawings.

With reference to FIG. 1, it is seen that the artificial kidney according to the present invention incorporates an exchanger 1 of any known type, comprising at least two compartments 3 and 4 separated by a semipermeable membrane 2. The first compartment 3 is connected to a patient (not shown) via an extracorporeal blood circuit 5, whereas a dialysis fluid circuit 6 passes through the second compartment 4. By way of example and not limitation, a suitable exchanger 1 for use with the present invention may be a BIOSPAL or FILTRAL exchanger, manufactured by HOSPAL INDUSTRIE, avenue Lionel Terray, Meyzieu, France.

This dialysis fluid circuit 6 incorporates, upstream from the exchanger 1, in a conventional manner, a device 10 for preparing the dialysis fluid, which is connected to a source of concentrate (not shown) as well as to a water supply (not shown). The conductivity of the dialysis fluid at inflow to the exchanger may be monitored by means of the conductimeter 7. By way of example and not limitation, a suitable conductimeter 7 may be a carbon conductivity cell having a constant $K = 1.0 \pm 0.5\%$ sold by the Kent Society of France.

A second conductimeter 8 measures the conductivity of the dialysis fluid at outflow from the exchanger 1 before it is led to means for discharging or recycling (not shown).

The dialysis fluid circuit 6 incorporates, in addition, although they are not shown for reasons of clarity, all the components required for correct circulation of the dialysis fluid: pumps, flowmeters, outgassing devices, blood detectors, valves, and the like, which are not of decisive importance in relation to the present invention.

The conductimeters 7 and 8 are connected to a monitoring device 9, which is also connected to the dialysis fluid preparation device 10. By way of example and not limitation, a suitable monitoring device 9 may be a M68HC 11 manufactured by MOTOROLA-USA.

Figure 2:
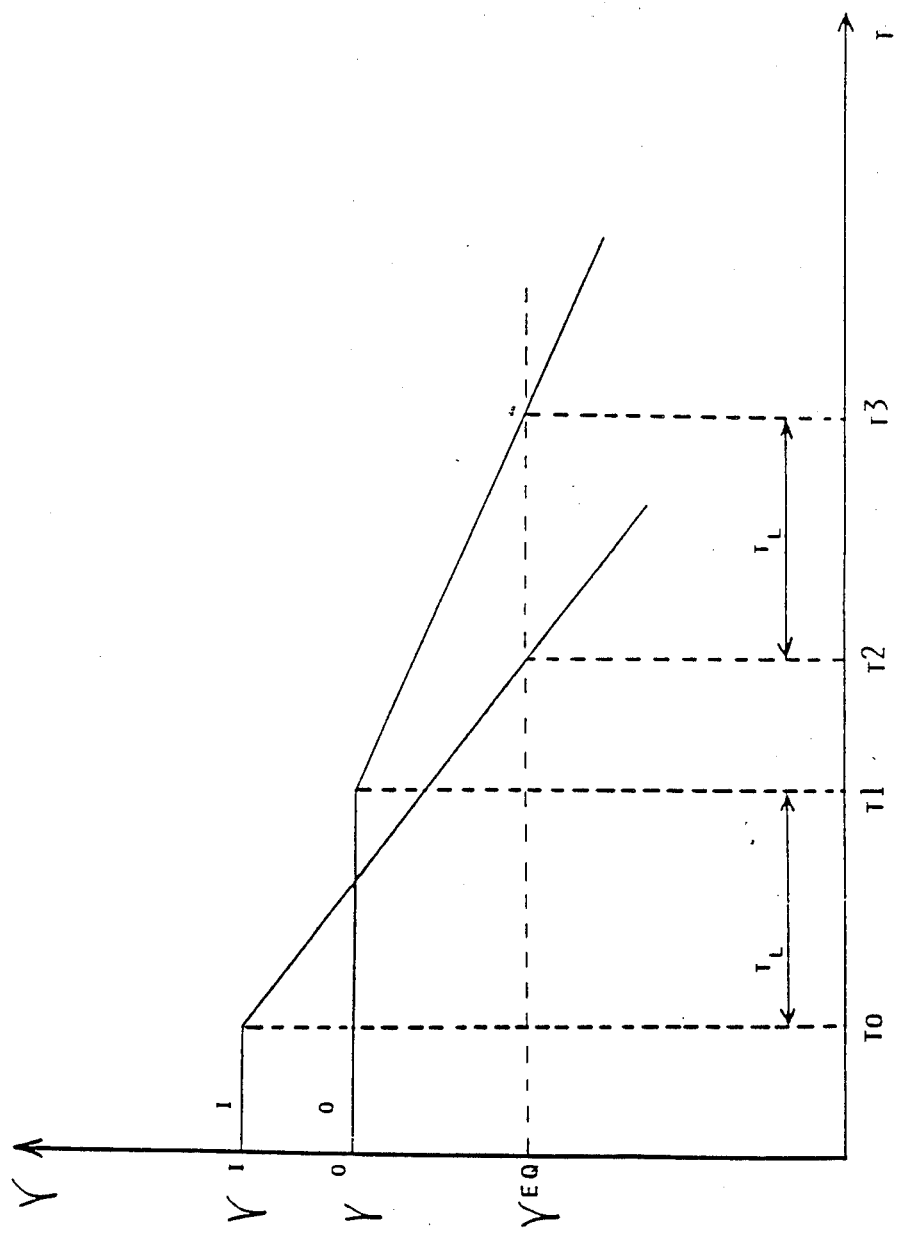
FIG. 2 is a graphic representation of an embodiment of the method which is the subject of the present invention.

The method for determining the conductivity of the dialysis fluid in equilibrium with the plasma is illustrated in FIG. 2. This figure shows changes with respect to time in the conductivity of the dialysis fluid at inflow to the exchanger (curve 1) as well as the changes with respect to the time in the conductivity of the dialysis fluid at outflow from the exchanger (curve 0). The time period shown here is the time period corresponding to the measurement.

The values for the curve 0 are the values measured by means of the conductimeter 8. The values for the curve 1 are either the conductivity values measured by the conductimeter 7, or the conductivity values fixed in advance by the monitoring device 9 or by any other device enabling the conductivity of the dialysis fluid prepared by the device 10 to be selectively determined.

The determination of the conductivity of the dialysis fluid in equilibrium with the plasma will, however, be more accurate if the values adopted for plotting the curve 1 are the values effectively measured at inflow to the exchanger by the conductimeter 7, this being the case chosen for the description which follows.

Thus, at the point when it is desired to take a measurement, a specified change in the conductivity of the dialysis fluid at inflow to the exchanger is imposed by means of an action of the monitoring device 9 on the preparation device 10. This is possible by virtue of a dialysis fluid generator capable of supplying a liquid whose sodium concentration is variable.

The consequence of this action is a change in the conductivity of the dialysis fluid measured by the conductimeter 7, starting at the instant $t_0$, which is reflected in the curve 1 by a change in slope.

Observation of the curve 0 shows that, while the conductivity at inflow to the exchanger begins to change from the instant $t_0$, the conductivity of the dialysis fluid at outflow from the exchanger, which is measured by the conductimeter 8, begins to change only from the instant $t_1$. The time interval separating the instant $t_0$ from the instant $t_1$ is the lag time $t_L$, which is the length of time needed for a change in the conductivity measured by the conductimeter 7 to bring about a change in the conductivity measured by the conductimeter 8. The lag time $t_L$ is determined according to a method which will be explained below.

The monitoring device 9 determines the conductivity of the dialysis fluid in equilibrium with the plasma by comparing, for each value of the conductivity of the dialysis fluid measured at outflow from the exchanger 1 by the conductimeter 8 at an instant t, the corresponding conductivity value at inflow to the exchanger, that is to say the value measured by the conductimeter 7 at the instant $t' = t - t_L$. The conductivity for which these two values are equal is the conductivity of the dialysis fluid in equilibrium with the plasma.

Thus, in FIG. 2, the conductivity of the dialysis fluid at equilibrium $\gamma_{EQ}$ is the conductivity measured by the conductimeter 8 at the instant $t_3$, which is equal to the conductivity measured by the conductimeter 7 at the instant $t_2 = t_3 - t_L$.

In effect, since the conductivity of the dialysis fluid varies essentially according to its sodium concentration, it is considered that, if the conductivity of the dialysis fluid does not change during its passage through the exchanger, it is the case that the sodium concentration does not change either. Accordingly, equilibrium is considered to be achieved between the dialysis fluid circulating on one side of membrane 2 and the blood plasma circulating on the other side of membrane 2.

From this value for the conductivity of the dialysis fluid at equilibrium, it is then possible to determine the patient's blood sodium level. The relationship between these two values can be calculated in two stages: in the first place, conversion of the conductivity of the dialysis fluid to sodium concentration, and then to blood sodium level.

The very good correlation existing between the sodium concentration in the dialysis fluid and the conductivity measurement is illustrated in the last chapter of Dr. Petitclerc's thesis already cited. In effect, sodium represents, with the anion which necessarily accompanies it in order to provide for electrical neutrality, approximately 95% of the ionic osmolality of the dialysis fluid. Thus, by taking temperature variations into account, it is possible to follow sodium changes in the dialysis fluid by means of conductivity measurements.

The second stage of the calculation is the determination of the blood sodium level from the sodium concentration in the dialysis fluid. Since the sodium is an electrically charged particle, the ratio of the sodium concentrations on each side of the membrane is equal to the Donnan coefficient. This relationship has been described by Dr. Petitclerc in an article entitled "Clinical Validation of a Predictive Modeling Equation for Sodium" (Artificial Organs, Vol. 9, No. 2, 1985), incorporated herein by reference.

The relationship between the conductivity of the dialysis fluid at equilibrium and the blood sodium level can be established directly on the basis of the results published in Chapter 6 (FIG. 5 and page 156) of Dr. Petitclerc's thesis cited above, showing the good correlation existing between the conductivity of the dialysis fluid at equilibrium and the effective sodium concentration which is known to be equivalent to the blood sodium level.

Figure 3:
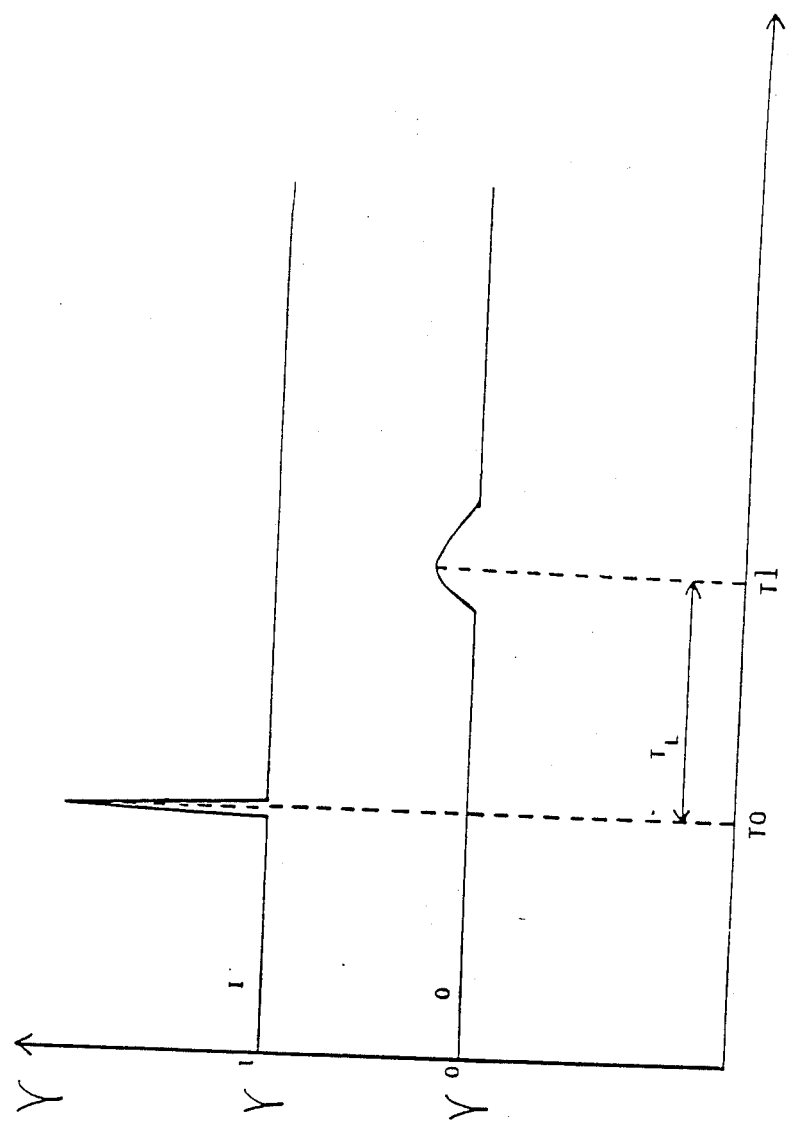
FIG. 3 is a graphic representation of the determination of the lag time $t_L$ according to an embodiment of the present invention.

FIG. 3 illustrates the determination, according to a second embodiment of the present invention, of the lag time $t_L$, which is the length of time needed for a change in the conductivity imposed at inflow to the exchanger to bring about a change in the conductivity measured by the conductimeter 8.

If, in order to determine the conductivity of the dialysis fluid in equilibrium with the plasma, the value measured by the conductimeter 7 is chosen as the conductivity value at inflow to the exchanger, the lag time $t_L$ is then the length of time needed for a change in conductivity measured by the conductimeter 7 to bring about a change in the value measured at outflow from the exchanger by the conductimeter 8. This is the case described below.

In a second embodiment of the method of the present invention where the values set in advance by the monitoring device are chosen as the conductivity value at inflow to the exchanger, the lag time $t_L$ is the length of time separating the value for the change in the conductivity specified by the monitoring device 9 and the change in conductivity measured by the conductimeter 8.

The curve 1 of FIG. 3 shows, in the same way as in FIG. 2, the time-course of the changes in the conductivity of the dialysis fluid at inflow to the exchanger, whereas the curve 0 shows the time-course of the changes in the conductivity of the dialysis fluid at outflow from the exchanger.

To accomplish this determination of the lag time $t_L$, a large but brief change is imposed on the conductivity of the dialysis fluid prepared in device 10, which is reflected in the curve 1 by a conductivity peak which is detected at the instant $t_0$ by means of conductimeter 7.

The time elapsing between the instant $t_0$ and the instant $t_1$, at which the change in conductivity of the dialysis fluid at outflow from the exchanger is detected by means of the conductimeter 8, is then measured, this change being the response to the change in conductivity produced at inflow to the exchanger. The time separating the instant $t_0$ from the instant $t_1$ is equal to the lag time $t_L$.

Figure 4:
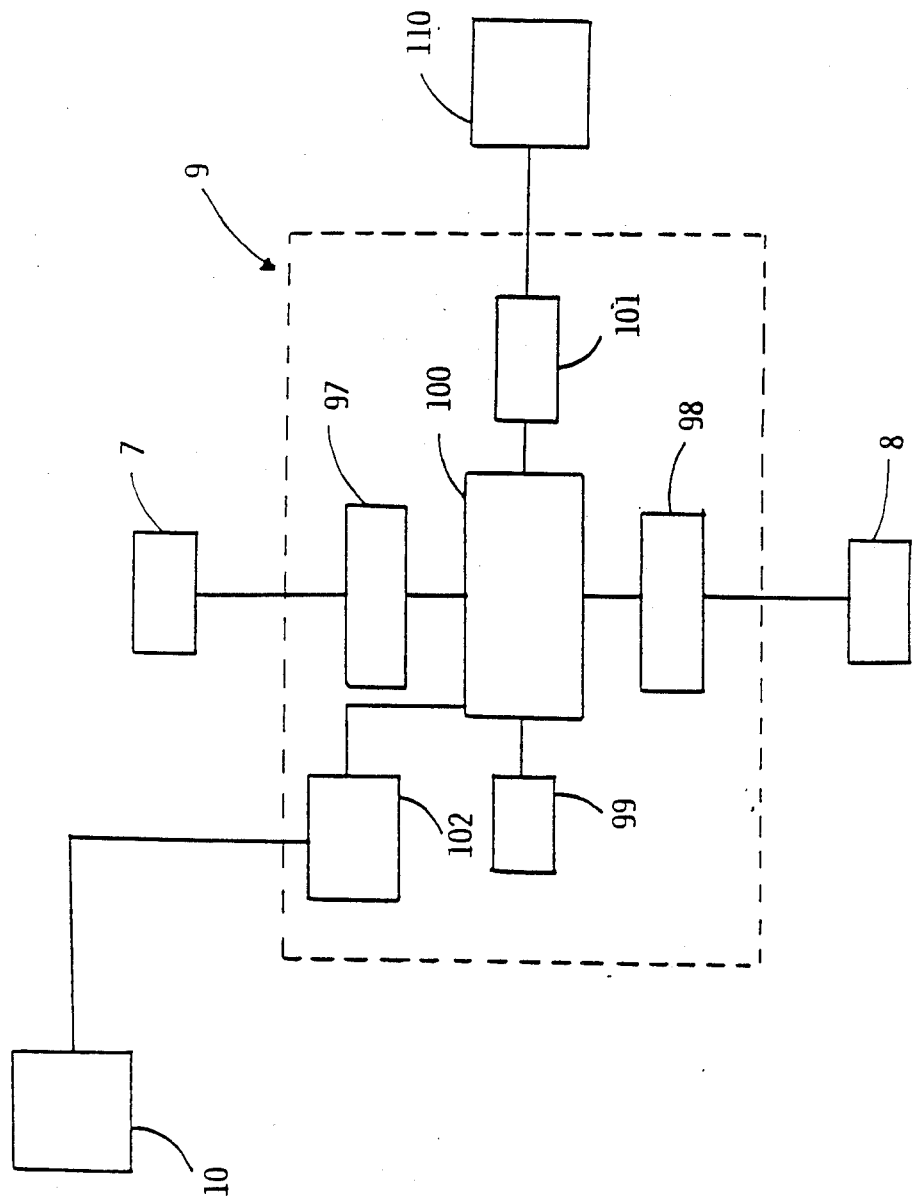
FIG. 4 is a representation in the form of a block diagram of the monitoring device of the present invention.

In order to enable the different stages of the method described above to be carried out, the artificial kidney which is the subject of the present invention incorporates a monitoring device 9 whose different functions are illustrated in the form of a block diagram in FIG. 4. The information derived from the conductimeters 7 and 8 is received by the monitoring device 9 by virtue of receptor members 97 and 98, respectively. These receptor members consist, for example, of memories, connected to a computer 100. From the information stored in these members 97 and 98, the computer 100 determines the value of the lag time $t_L$ which is then stored at 99, and also determines the conductivity value of the dialysis fluid in equilibrium with the plasma, which is the value for which the conductivity of the dialysis fluid at outflow from the exchanger at an instant t is equal to the conductivity of the dialysis fluid at inflow to the exchanger at an instant $t' = t - t_L$.

This value for the conductivity of the dialysis fluid in equilibrium with the plasma is then transmitted to a converter 101, which then determines the value for the corresponding blood sodium level.

In order to be accessible to the doctor supervising the haemodialysis session, it is possible to provide means 110 for displaying the result of the measurement.

The monitoring device 9 also incorporates a system 102 for controlling the change in conductivity of the dialysis fluid. This control system 102 acts on the preparation device 10 and is advantageously connected to the computer 100. Preferably, the monitoring device 9 is a microcontroller.

Figure 5:
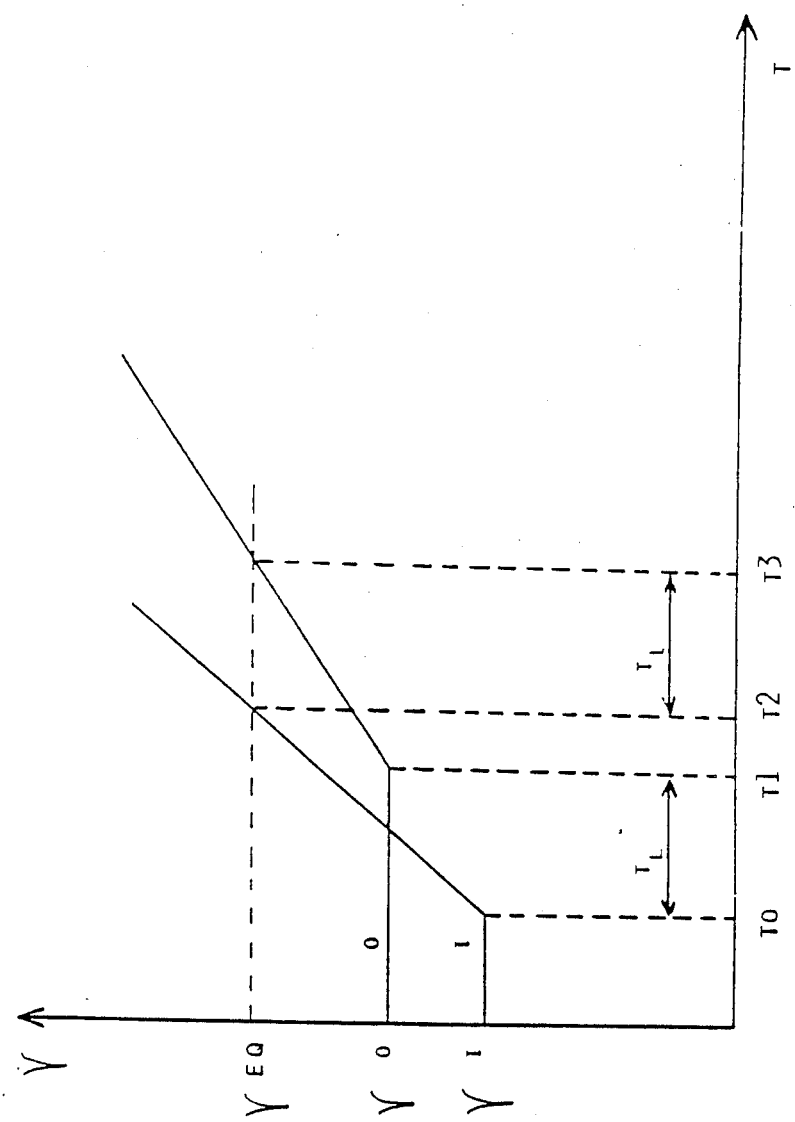
FIGS. 5 and 6 illustrate other embodiments of the present invention.

According to another embodiment of the present invention, as illustrated in FIG. 5, the conductivity of the dialysis fluid at inflow to the exchanger is changed, not in a decreasing manner, but in an increasing manner.

The change in conductivity has been shown in FIGS. 2 and 5 occuring in a continuous manner. It is also possible to change the conductivity in a discontinuous manner, by successive steps.

According to another embodiment of the present invention, the determination of the lag time $t_L$ is performed retrospectively, after storage of the conductivity values at outflow from the exchanger has begun. In effect, the different values measured by means of the conductimeter 8 are held in storage and the equation for the curve 0 is determined as soon as the number of measurements is sufficient.

Since the conductivity of the dialysis fluid at outflow from the exchanger is constant up to the instant $t_1$, it is possible to determine $t_1$, which is the abscissa of the point at which the slope of the curve 0 changes. Thus, $t_1$ is readily determined by calculating the abscissa of the point satisfying the equation for 0 and whose ordinate is the conductivity value measured by means of the conductimeter 8 before the measuring period begins. When $t_1$ is determined, it is easy to calculate lag time $t_L$ which is the time between $t_0$ and $t_1$.

Figure 6:
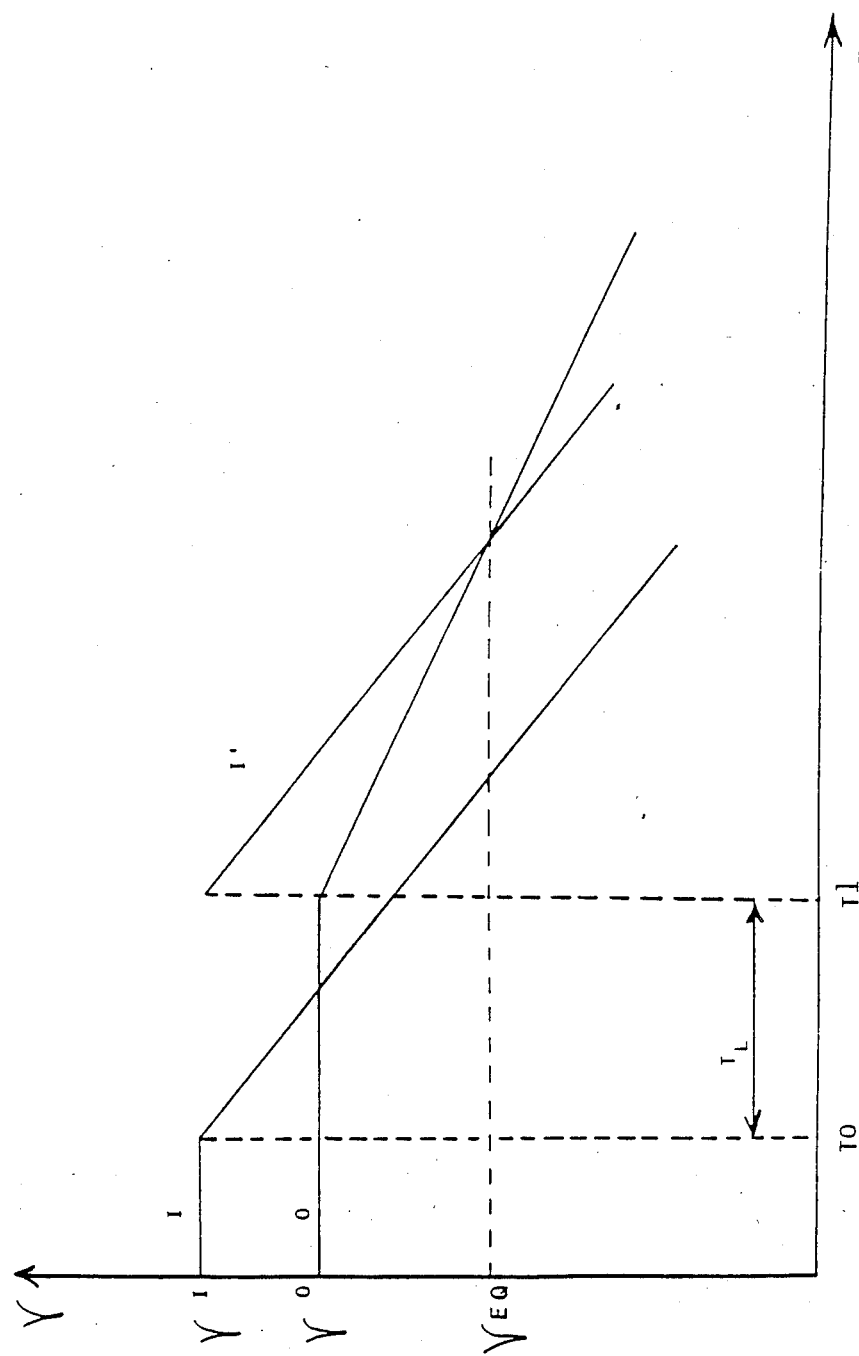

According to another embodiment of the present invention, as illustrated in FIG. 6, the conductivity of the dialysis fluid at equilibrium is determined by translating the curve I in time through a distance $t_L$. The curve I' is then obtained. Once the equation for the curves I' and 0 is determined, the value for the conductivity of the dialysis fluid at equilibrium is the ordinate of the point of intersection of the curves I' and 0.

Additional advantages and modifications will readily occur to those skilled in the art. The invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A method for determining the blood sodium level of a patient whose blood circulates through a first compartment of an exchanger of an artificial kidney, said first compartment being separated from a second compartment of the exchanger by a semipermeable membrane for permitting dialysis and ultrafiltration of the blood, said second compartment being disposed in a dialysis fluid circuit through which dialysis fluid passes, comprising the steps of:

changing, in a selected manner, the conductivity of the dialysis fluid flowing into the second compartment of the exchanger;

measuring, in response to the step of changing the conductivity of the dialysis fluid, the change in conductivity of the dialysis fluid flowing out of the second compartment of the exchanger;

determining a lag time $t_L$ between the change in conductivity of the dialysis fluid flowing into the second compartment of the exchanger and the corrresponding measured change in conductivity of dialysis fluid flowing out of the second compartment of the exchanger;

determining an equilibrium conductivity value of the dialysis fluid in the second compartment of the exchanger for which the conductivity of the dialysis fluid at outflow from the second compartment at a time t is substantially equal to the conductivity of the dialysis fluid at inflow into the second compartment at a time $t' = t - t_L$; and determining the sodium concentration in the patient's blood in accordance with the determined equilibrium conductivity value.

2. The method according to claim 1, wherein the step of changing the conductivity of the dialysis fluid flowing into the second compartment of the exchanger includes the substep of:

increasing the conductivity of the dialysis fluid flowing into the second compartment in a predetermined manner.

3. The method of claim 1, wherein the step of changing the conductivity of the dialysis fluid flowing into the second compartment of the exchanger includes the substep of:

decreasing the conductivity of the dialysis fluid flowing into the second compartment in a predetermined manner.

4. The method of claims 2 or 3 wherein the conductivity of the dialysis fluid flowing into the second compartment of the exchanger is changed in a substantially continuous manner.

5. The method of claim 1, wherein the conductivity of the dialysis fluid is changed in a stepwise manner for a predetermined brief period of time beginning at time $t_o$, said lag time $t_L$ then corresponding to the difference between the time $t_0$ and a time $t_1$ corresponding to initialization of the measured change in conductivity of dialysis fluid flowing out of the second compartment.

6. The method of claims 1, 2, or 3, wherein the step of determining the lag time $t_L$ includes the substeps of:

determining a time to corresponding to the initialization of the change in conductivity of the dialysis fluid flowing into the second compartment of the exchanger;

monitoring, as a function of time, changes in the conductivity of the dialysis fluid flowing out of the second compartment to determine a time $t_1$ corresponding to the initialization of the change in conductivity of dialysis fluid flowing out of the second compartment;

determining the lag time $t_L$ in accordance with the interval between times $t_l$ and $t_o$.

7. The method of claims 1, 2, 3, or 5, wherein the artificial kidney includes a conductimeter positioned in the dialysis fluid circuit upstream of the second compartment of the exchanger relative to the flow of dialysis fluid in the dialysis fluid circuit, and wherein the method includes the further step of measuring, with the conductimeter, the conductivity of the dialysis fluid flowing into the second compartment.

8. The method of claims 1, 2, 3, or 5, wherein the artificial kidney includes a monitoring device including means for changing the conductivity of the dialysis fluid flowing into the second compartment in accordance with a predetermined pattern, and wherein the step of changing the conductivity of the dialysis fluid flowing into the second compartment includes the substep of monitoring, with the monitoring means, the predetermined pattern of the changing means to determine the conductivity of the dialysis fluid flowing into the second comparment of the exchanger.

9. A method for determining the blood sodium level of a patient's blood circulating through a first compartment of an exchanger of an artificial kidney, said exchanger including a semipermeable membrane separating the first compartment from a second compartment of the exchanger through which dialysis fluid in a dialysis fluid circuit passes, said membrane being adapted to permit the dialysis and ultrafiltration of the blood from between the first and second compartments, comprising the steps of:

selectively changing the conductivity of dialysis fluid flowing into the second compartment of the exchanger;

monitoring the conductivity of the dialysis fluid flowing into the second compartment to determine a time $t_o$ at which the conductivity of the dialysis fluid flowing into the second compartment changes in response to the step of selectively changing the conductivity;

monitoring the conductivity of the dialysis fluid flowing out of the second compartment to determine a time $t_l$ at which the conductivity of the dialysis fluid flowing out of the second compartment changes in response to the step of selectively changing the conductivity;

determining a lag time $t_L$ between initialization of the change in conductivity of the dialysis fluid flowing into and out of the second compartment in accordance with the difference between the times $t_0$ and $t_1$;

determining an equilibrium value between the conductivity of the dialysis fluid in the second compartment and the conductivity of the blood in the first compartment in accordance with the monitored values of conductivity of the dialysis fluid and the lag time $t_L$; and determining the patient's blood sodium level in accordance with the determined equilibrium conductivity value.

10. The method of claim 9, wherein the step of determining an equilibrium value of conductivity includes the substep of:

determining a value of conductivity of the dialysis fluid flowing out the second compartment at a time $t_3$ which conductivity value is substantially equal to a value of conductivity of the dialysis fluid flowing into the second compartment at a time $t_2 = t_3 - t_L$, said conductivity value of the dialysis fluid at the times $t_2$ and $t_3$ substantially corresponding to the equilibrium value of conductivity of the patient's blood and the dialysis fluid.

11. An artificial kidney including an exchanger having at least first and second compartments separated by a semipermeable membrane for permitting the dialysis and ultrafiltration of the blood therethrough, said first compartment being disposed in an extracorporeal blood circuit and said second compartment having an inlet and an outlet for flow communicating with a dialysis fluid circuit having dialysis fluid flowing therethrough, comprising:

means for selectively changing the conductivity of the dialysis fluid flowing into said second compartment through said inlet;

means for measuring the conductivity of the dialysis fluid flowing out of said second compartment through said outlet;

means for determining a lag time $t_L$ between a change in conductivity of the dialysis fluid flowing into said second compartment and a corresponding change in conductivity of the dialysis fluid flowing out of said second compartment;

means for determining an equilibrium conductivity value of the dialysis fluid relative to the blood for which value the conductivity of the dialysis fluid at outflow from said second compartment at an instant t is equal to the conductivity of the dialysis fluid at inflow to said second compartment at an instant $t' = t - t_L$.

12. The artificial kidney of claim 11, including means for monitoring the conductivity of the dialysis fluid flowing into said second compartment.

13. The artificial kidney of claims 11 or 12, including means for determining a value of the blood sodium level in accordance with said equilibrium conductivity value of the dialysis fluid and the blood.

14. The artificial kidney of claims 11 or 12, wherein said means for determining the lag time $t_L$, and said means for determining the equilibrium conductivity value of the dialysis fluid and the blood comprise a microcontroller.

15. The artificial kidney of claim 13, wherein said means for determining a value of the blood sodium level comprises a microcontroller.

* * * * *